United States Patent
Emerson (10) Patent No.: US 11,517,701 B1
(45) Date of Patent: Dec. 6, 2022

(54) OXYGEN DELIVERY DEVICE

(71) Applicant: Neale Emerson, Venice, FL (US)

(72) Inventor: Neale Emerson, Venice, FL (US)

(*) Notice: Subject to any disclaimer, the term of this patent is extended or adjusted under 35 U.S.C. 154(b) by 551 days.

(21) Appl. No.: 16/687,908

(22) Filed: Nov. 19, 2019

Related U.S. Application Data (63) Continuation-in-part of application No. 16/174,390, filed on Oct. 30, 2018, now Pat. No. 10,967,203.

(51) Int. Cl.
*A61M 16/08* (2006.01)
*A61M 16/20* (2006.01)

(52) U.S. Cl.
CPC ...... *A61M 16/0875* (2013.01); *A61M 16/201* (2014.02); *A61M 2202/0208* (2013.01)

(58) Field of Classification Search
CPC ............ A61M 16/0875; A61M 16/201; A61M 2202/0208; A62B 7/02; A62B 25/00; A62B 7/00; A62B 9/02; Y10T 137/6851; Y10T 137/2544; Y10T 137/7838
USPC ............ 128/205.24, 205.25, 203.11, 204.28, 128/202.28, 205.19, 205.22, 205.23, 128/207.11, 200.21, 201.27, 201.28, 128/202.22, 202.29, 203.25, 204.18, 128/204.21, 204.26, 205.11, 205.13, 128/205.14, 205.15, 205.16, 205.17, 128/206.15, 207.12, 207.18; 222/6, 71, 222/173
See application file for complete search history.

(56) References Cited

U.S. PATENT DOCUMENTS

| | | | | |
|---|---|---|---|---|
| 3,696,964 A | * | 10/1972 | Deakin | F17C 13/06 220/727 |
| 3,717,147 A | * | 2/1973 | Flynn | A61M 16/127 128/204.25 |
| 3,726,274 A | * | 4/1973 | Bird | A61M 16/127 128/205.24 |
| 4,054,133 A | | 10/1977 | Myers | |
| 4,579,114 A | | 4/1986 | Gray | |
| 4,798,203 A | * | 1/1989 | Bartos | A62B 7/02 128/205.24 |
| 5,121,745 A | | 6/1992 | Israel | |
| 5,299,565 A | | 4/1994 | Brown | |
| 5,396,885 A | | 3/1995 | Nelson | |

(Continued)

FOREIGN PATENT DOCUMENTS

WO 0234338 2/2002

*Primary Examiner* — Elliot S Ruddie
(74) *Attorney, Agent, or Firm* — Kyle A. Fletcher, Esq.

(57) ABSTRACT

The adapter for an oxygen delivery device is a continuation-in-part application configured for use with a previously disclosed oxygen delivery device. The adapter for an oxygen delivery device is modified to work with a single oxygen canister. The adapter for an oxygen delivery device attaches to the single oxygen canister. The adapter for an oxygen delivery device is configured for use with the distribution apparatus of the prior disclosure. The adapter for an oxygen delivery device comprises a canister adapter and a manual flow valve. The canister adapter is a mechanical structure that offsets the distribution apparatus such that the distribution apparatus will receive oxygen from the single oxygen canister. The manual flow valve is a plunger valve that attaches to the distribution apparatus. The manual flow valve controls the flow of oxygen into the distribution apparatus from the canister adapter.

16 Claims, 4 Drawing Sheets

(56) References Cited

U.S. PATENT DOCUMENTS

| | | | |
|---|---|---|---|
| 5,429,152 A * | 7/1995 | Van Straaten | F17C 13/06 220/726 |
| 5,469,842 A | 11/1995 | Flynn | |
| 5,647,346 A | 7/1997 | Holscher | |
| 5,676,135 A | 10/1997 | McClean | |
| 6,354,294 B1 | 3/2002 | Villareal, Jr. | |
| 7,360,538 B2 | 4/2008 | Flynn | |
| 2005/0085799 A1 | 4/2005 | Luria | |

\* cited by examiner

OXYGEN DELIVERY DEVICE

CROSS REFERENCES TO RELATED APPLICATIONS

This non-provisional application is a continuation-in-part application filed under 37 CFR 1.53(b) that claims the benefit of United States 35 USC 120 from non-provisional application U.S. Ser. No. 16/174,390 filed on Oct. 30, 2018 by the inventor: Neale Emerson. This non-provisional application incorporates non-provisional application U.S. Ser. No. 16/174,390 in its entirety.

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of life-saving equipment including a respiratory apparatus further comprising compressed oxygen. (A62B7/02)

This non-provisional application is a continuation-in-part application filed under 37 CFR 1.53(b) that claims the benefit of United States 35 USC 120 from non-provisional application U.S. Ser. No. 16/174,390 filed on Oct. 30, 2018 by the inventor: Neale Emerson. This non-provisional application incorporates non-provisional application U.S. Ser. No. 16/174,390 in its entirety.

The present disclosure will only reference the elements of the non-provisional application U.S. Ser. No. 16/174,390 that are relevant to the innovations disclosed within this application. This is done for purposes of simplicity and clarity of exposition. The applicant notes that this disclosure incorporates non-provisional application U.S. Ser. No. 16/174,390 in its entirety into this application. The fact that any specific innovation selected from the one or more innovations disclosed within U.S. Ser. No. 16/174,390 is not addressed in this application should not be interpreted as an indication of defect in the above referenced patent.

Within this disclosure, the non-provisional application U.S. Ser. No. 16/174,390 will also be referred to as the prior disclosure.

A summary of the disclosures contained within the prior disclosure that are relevant to the present disclosure is provided below. This summary is provided for clarity and convenience and is not intended to fully represent or reflect the disclosures contained within the prior disclosure. If a discrepancy occurs between this summary and the prior disclosure, the prior disclosure should be considered correct and this summary should be considered in error.

The prior disclosure discloses an oxygen delivery device. The oxygen delivery device is a portable structure. The oxygen delivery device contains a plurality of oxygen canisters. The plurality of oxygen canisters contain oxygen under pressure. The oxygen delivery device stores the plurality of oxygen canisters. The oxygen delivery device dispenses the oxygen contained in the plurality of oxygen canisters. The oxygen delivery device comprises a housing, a distribution apparatus and the plurality of oxygen canisters. The housing contains the plurality of oxygen canisters. The distribution apparatus attaches to the housing and the plurality of oxygen canisters. The housing: a) stores the plurality of oxygen canisters; and, b) forms a fluidic connection between the plurality of oxygen canisters and the distribution apparatus. The distribution apparatus delivers the oxygen received from the plurality of oxygen canisters to a patient for consumption.

The distribution apparatus is a fluid transport structure. The distribution apparatus delivers oxygen in a gas phase from a plurality of oxygen canisters to the patient. The distribution apparatus comprises a mask, a hose, and an oxygen connector.

The mask physically delivers oxygen in a gas phase directly to the patient. The hose is a fluid transport structure. The hose is a commercially available flexible tubing that transports oxygen from the plurality of oxygen canisters to the oxygen connector. The oxygen connector forms a fluidic connection between the mask and the hose. The oxygen connector is a rigid structure. The oxygen connector is a hollow structure. The oxygen connector comprises a bellows connection and a feed/exhaust structure.

The bellows connection is a tube that inserts into the mask. The bellows connection is configured for emergency use. The end of the bellows connection that is distal from the mask is normally closed. The end of the bellows connection that is distal from the mask can open to the atmosphere. The bellows connection is sized to receive a bellows. The bellows is a manually operated pump used by emergency services personnel. The bellows forces fresh atmospheric gas to the point of consumption in an emergency situation.

The feed/exhaust structure is a mechanical structure that: a) feeds the oxygen in a gas phase to the patient; and, b) discharges exhalation gases generated by the patient. The feed/exhaust structure is a tubular structure. The feed/exhaust structure branches off of the bellows connection. The feed/exhaust structure further comprises an exhaust port and a feed valve.

The exhaust port is a port through which the exhaust gases are discharged from the feed/exhaust structure. The exhaust port is a check valve that mounts on the end of the tubular structure of the feed/exhaust structure that is distal from the mask. The exhaust port opens under exhalation pressure to release the exhaled gases.

The feed valve is a port through which the oxygen in a gas phase feeds into the feed/exhaust structure for transport to the mask. The feed valve is a check valve that mounts through the lateral face of the tubular structure of the feed/exhaust structure. The oxygen in a gas phase flows through the feed valve and the feed/exhaust structure to the mask. The feed valve opens in response to an inhalation vacuum to allow the flow of oxygen in a gas phase into the feed/exhaust structure.

The distribution apparatus attaches to the plurality of oxygen canisters through the manifold plate. The manifold plate is a fluidic connection that: a) receives the oxygen in a gas phase from each of the plurality of oxygen canisters; b) aggregates the oxygen in a gas phase received from the plurality of oxygen canisters through a fluidic network; and, c) transports and releases the aggregated oxygen in a gas phase through an outlet fitting into the distribution apparatus.

One of the shortcomings of the prior disclosure is that the distribution can only form a fluidic connection to the plurality of oxygen canisters using the manifold plate. This prevents a patient from using the distribution apparatus to access oxygen from the alternate oxygen sources that are often available in medical facilities.

Clearly, a method to use the distribution apparatus to access alternate sources of oxygen would be of benefit.

SUMMARY OF INVENTION

The adapter for an oxygen delivery device addresses the shortcomings of the prior disclosure that are addressed above.

The adapter for an oxygen delivery device is a mechanical structure. The adapter for an oxygen delivery device is configured for use with a single oxygen canister. The single oxygen canister contains, stores, and dispenses oxygen under pressure. The adapter for an oxygen delivery device attaches to the single oxygen canister. The adapter for an oxygen delivery device is configured for use with the distribution apparatus of the prior disclosure. The adapter for an oxygen delivery device comprises a canister adapter and a manual flow valve. The canister adapter is a mechanical structure that offsets the distribution apparatus such that the distribution apparatus will receive oxygen from the single oxygen canister. The manual flow valve is a plunger valve that attaches to the distribution apparatus. The manual flow valve controls the flow of oxygen into the distribution apparatus from the canister adapter.

These together with additional objects, features and advantages of the adapter for an oxygen delivery device will be readily apparent to those of ordinary skill in the art upon reading the following detailed description of the presently preferred, but nonetheless illustrative, embodiments when taken in conjunction with the accompanying drawings.

In this respect, before explaining the current embodiments of the adapter for an oxygen delivery device in detail, it is to be understood that the adapter for an oxygen delivery device is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the adapter for an oxygen delivery device.

It is therefore important that the claims be regarded as including such equivalent construction insofar as they do not depart from the spirit and scope of the adapter for an oxygen delivery device. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

This non-provisional application is a continuation-in-part application filed under 37 CFR 1.53(b) that claims the benefit of United States 35 USC 120 from non-provisional application U.S. Ser. No. 16/174,390 filed on Oct. 30, 2018 by the inventor: Neale Emerson. This non-provisional application incorporates non-provisional application U.S. Ser. No. 16/174,390 in its entirety.

The present disclosure will only reference the elements of the non-provisional application U.S. Ser. No. 16/174,390 that are relevant to the innovations disclosed within this application. This is done for purposes of simplicity and clarity of exposition. The applicant notes that this disclosure incorporates non-provisional application U.S. Ser. No. 16/174,390 in its entirety into this application. The fact that any specific innovation selected from the one or more innovations disclosed within U.S. Ser. No. 16/174,390 is not addressed in this application should not be interpreted as an indication of defect in the above referenced patent.

Figure 1:
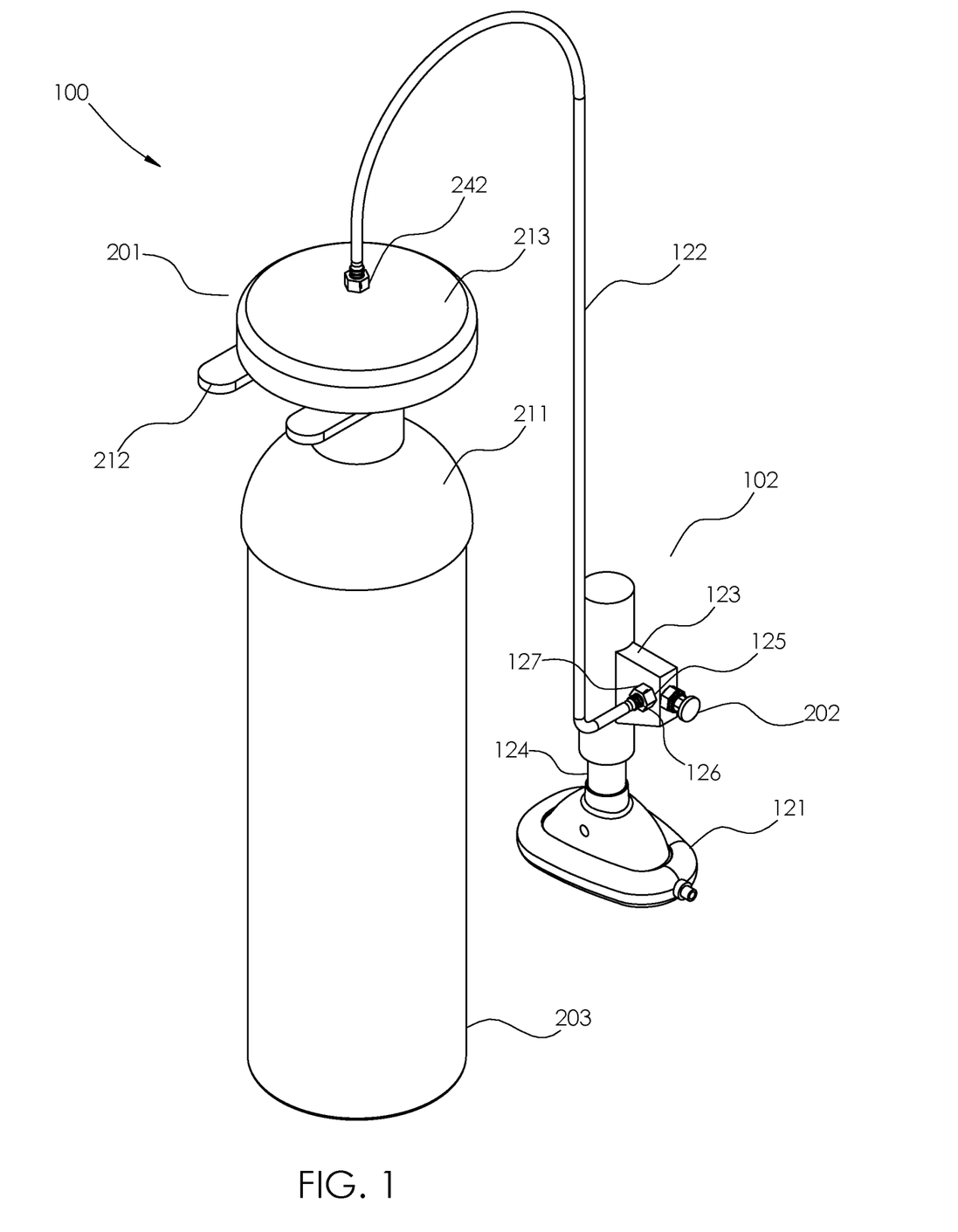
FIG. 1 is a perspective view of an embodiment of the disclosure.
Figure 2:
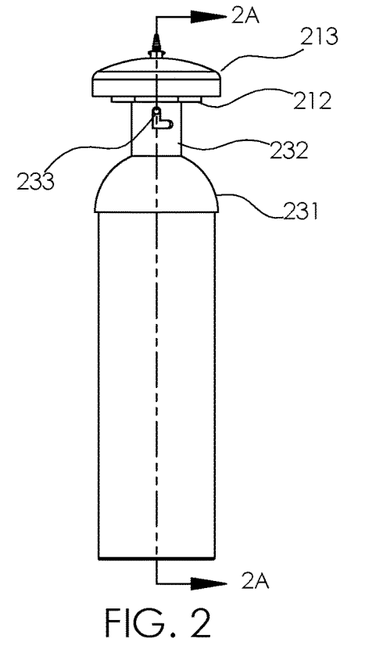
FIG. 2 is a front view of an embodiment of the disclosure.
Figure 2A:
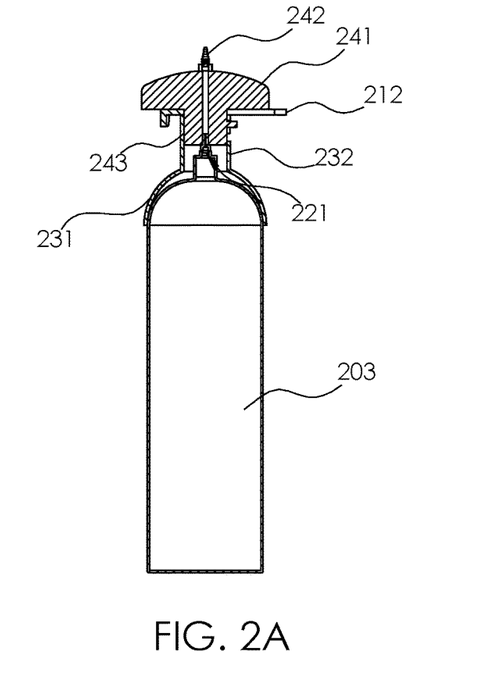
FIG. 2a is a cross-sectional view of an embodiment of the disclosure.
Figure 3:
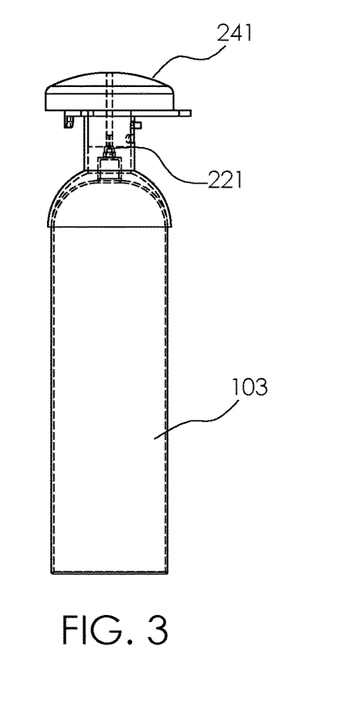
FIG. 3 is a side view of an embodiment of the disclosure.
Figure 4:
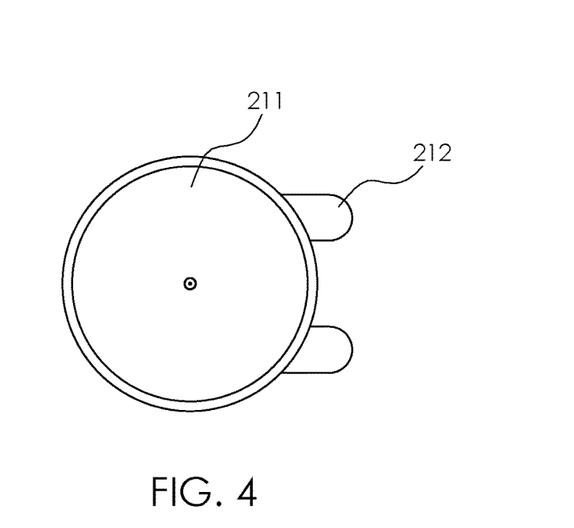
FIG. 4 is a top view of an embodiment of the disclosure.
Figure 5:
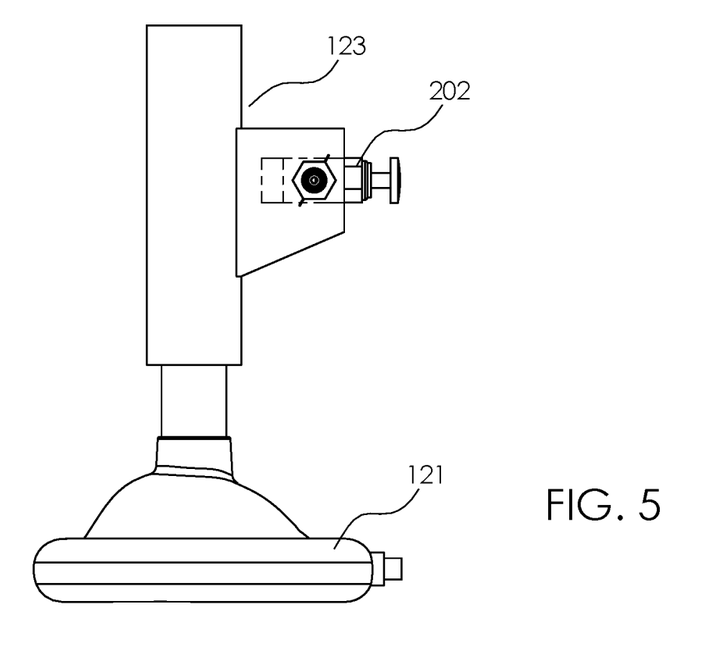
FIG. 5 is a side view of an embodiment of the disclosure.
Figure 6:
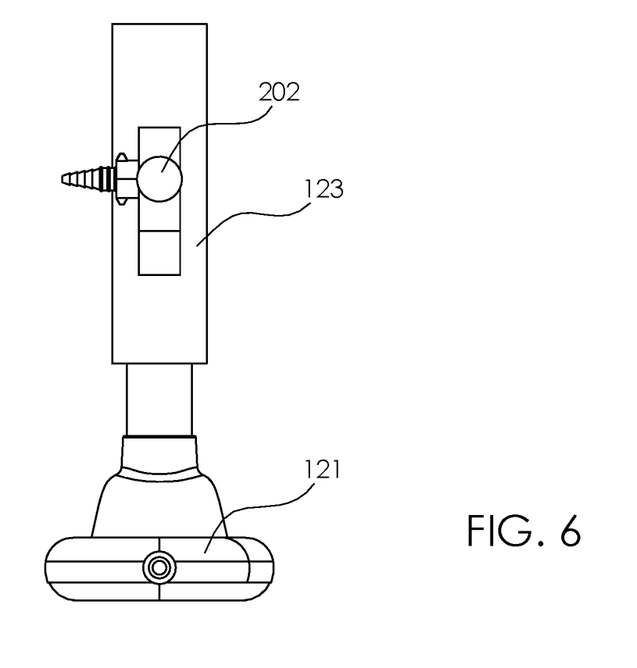
FIG. 6 is a detail view of an embodiment of the disclosure.
Figure 7:
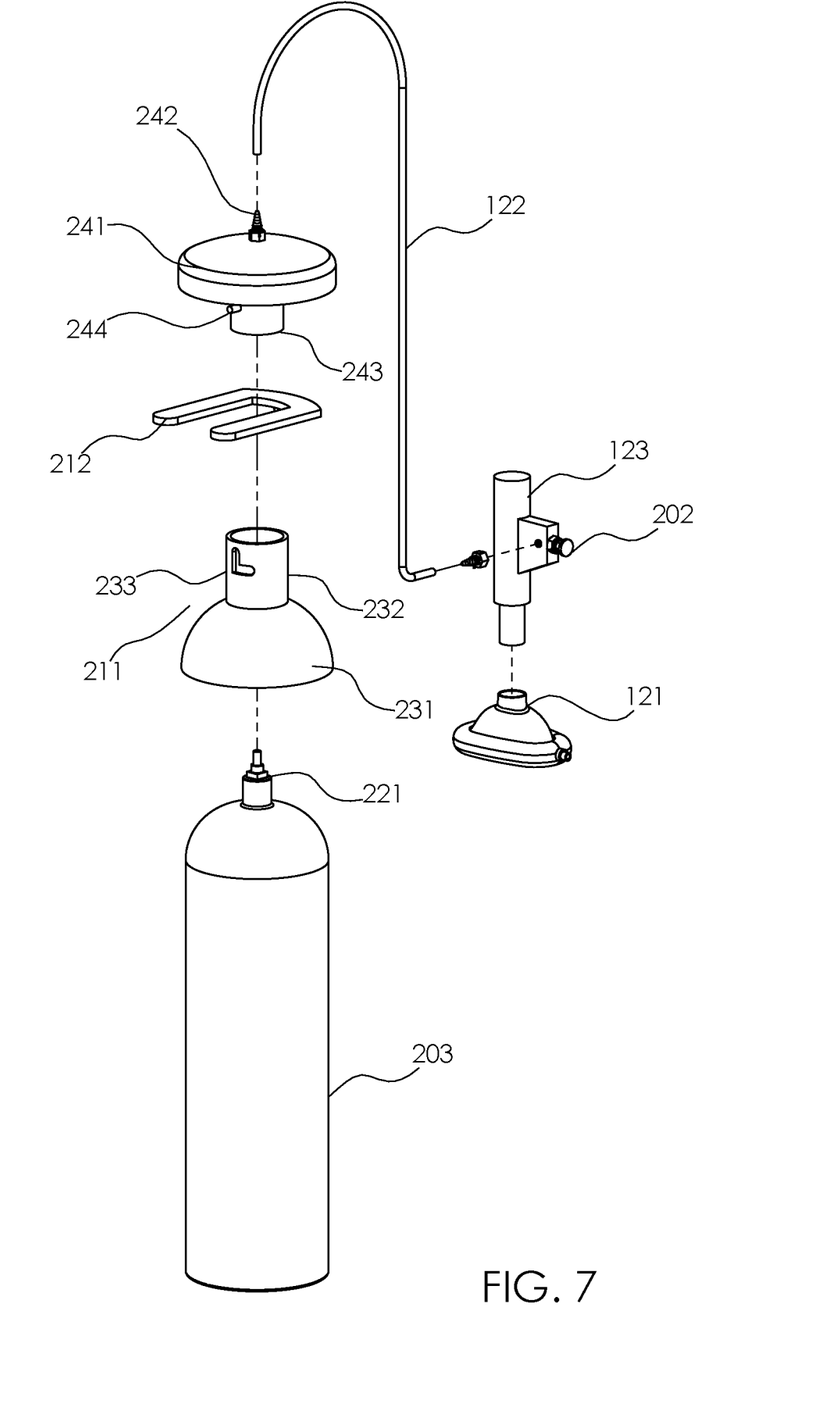
FIG. 7 is an exploded view of an embodiment of the disclosure.

Detailed reference will now be made to one or more potential embodiments of the disclosure, which are illustrated in FIGS. 1 through 7.

The adapter for an oxygen delivery device is a mechanical structure. The invention 100 is configured for use with a single oxygen canister 203. The single oxygen canister 203 contains, stores, and dispenses oxygen under pressure. The invention 100 attaches to the single oxygen canister 203. The invention 100 is configured for use with the distribution apparatus 102 of the prior disclosure. The invention 100 comprises a canister adapter 201 and a manual flow valve 202. The canister adapter 201 is a mechanical structure that interfaces with the distribution apparatus 102 such that the distribution apparatus 102 will receive oxygen from the single oxygen canister 203. The manual flow valve 202 is a plunger valve that attaches to the distribution apparatus 102. The manual flow valve 202 controls the flow of oxygen through the distribution apparatus 102.

The distribution apparatus 102 is a fluid transfer apparatus. The distribution apparatus 102 is provisioned through the prior disclosure. The distribution apparatus 102 is described in detail in the background section of this disclosure. The invention 100 is configured for use with the distribution apparatus 102 of the prior disclosure. The distribution apparatus 102 comprises a mask 121, a hose 122, and an oxygen connector 123.

The mask 121 physically delivers oxygen in a gas phase to a patient. The hose 122 forms a fluidic connection between the oxygen connector 123 and the single oxygen canister 203.

The oxygen connector 123 forms a physical connection between the hose 122 and the mask 121 such that oxygen will flow from the hose 122 into the mask 121. The oxygen connector 123 further comprises a bellows connection 124 and a feed/exhaust structure 125. The bellows connection 124 is a fluid transfer port that is formed in the mask 121. The bellows connection 124 provides access directly to the mask 121 for use with emergency medical equipment. The feed/exhaust structure 125 provides access directly to the mask 121 for use with emergency medical equipment. The feed/exhaust structure 125 further comprises an exhaust port 126 and a feed valve 127. The exhaust port 126 provides access directly to the feed/exhaust structure 125 for use with emergency medical equipment. The feed valve 127 provides access directly to the feed/exhaust structure 125 for use with emergency medical equipment.

The mask 121, the hose 122, the oxygen connector 123, the bellows connection 124, the feed/exhaust structure 125, the exhaust port 126, and the feed valve 127 are further described in the background section of this disclosure.

The single oxygen canister 203 is a high-pressure tank. The single oxygen canister 203 contains oxygen under pressure. The single oxygen canister 203 releases the oxygen into the canister adapter 201 of the invention 100. The form factor of the single oxygen canister 203 is a standardized structure. The single oxygen canister 203 further comprises a port fitting 221. The port fitting 221 is a commercially available fitting that controls the flow of oxygen into and out of the single oxygen canister 203.

The manual flow valve 202 is a valve. The manual flow valve 202 is a manually controlled structure. The manual flow valve 202 attaches to the oxygen connector 123 such that the manual flow valve 202 controls the flow of oxygen through the oxygen connector 123 from the hose 122 to the mask 121. The manual flow valve 202 allows the patient to manually control the amount of oxygen delivered to the patient.

The canister adapter 201 is a mechanical structure. The canister adapter 201 forms a fluidic interface that attaches the distribution apparatus 102 and the single oxygen canister 203. The canister adapter 201 adapts the distribution apparatus 102 for use with the single oxygen canister 203. The canister adapter 201 mechanically attaches directly to the single oxygen canister 203. The canister adapter 201 forms a fluidic connection with the single oxygen canister 203. The canister adapter 201 forms a fluidic connection with the hose 122 of the distribution apparatus 102. The canister adapter 201 further comprises a canister cap 211, a spacer 212, and an insert structure 213.

The canister cap 211 is a mechanical structure that adapts the canister adapter 201 to the form factor of the single oxygen canister 203. The canister cap 211 forms a shell that attaches to the single oxygen canister 203. The canister cap 211 attaches to the single oxygen canister 203 such that the canister cap 211 encloses the port fitting 221. The canister cap 211 further comprises a cover 231, a collar 232, and a locking aperture 233.

The cover 231 is a dome-shaped structure. The cover 231 is a hollow structure. The single oxygen canister 203 inserts into the cover 231 such that the cover 231 encloses a portion of the single oxygen canister 203 and fully encloses the port fitting 221.

The collar 232 is a prism-shaped structure. The collar 232 is a tubular structure. The collar 232 attaches the cover 231 to the insert structure 213. The insert structure 213 inserts into the collar 232 to attach to the canister cap 211.

The locking aperture 233 is an aperture that is formed through the lateral face of the prism structure of the collar 232. The locking aperture 233 forms an anchor point to which the insert structure 213 attaches to secure the insert structure 213 to the canister cap 211.

The spacer 212 is a mechanical structure. The spacer 212 is a disk-shaped structure. The disk shape of the spacer 212 has a u-shaped appearance. The spacer 212 separates the canister cap 211 from the insert structure 213 such that the span of the overall length of the canister adapter 201 can be adjusted to match the specific form factor of the single oxygen canister 203.

The insert structure 213 is a mechanical structure that attaches the canister cap 211 to the distribution apparatus 102 such that oxygen will flow from the port fitting 221 through the canister cap 211 and the insert structure 213 into the distribution apparatus 102. The insert structure 213 attaches to the canister cap 211 by inserting into the canister cap 211. The insert structure 213 further comprises a suspension disk 241, a supply fitting 242, and a collar 232 insert 243.

The suspension disk 241 is a plate structure. The suspension disk 241 is a disk-shaped structure. The suspension disk 241 forms the end of the insert structure 213 that is distal from the single oxygen canister 203.

The supply fitting 242 is a fitting that forms the fluidic connection between the canister adapter 201 and the hose 122 of the distribution apparatus 102. The supply fitting 242 mounts in the suspension disk 241 such that the supply fitting 242 is accessible from the exterior of the canister adapter 201.

The collar 232 insert 243 is a prism-shaped structure. The collar 232 insert 243 is a tubular structure. The collar 232 insert 243 is geometrically similar to the collar 232. The collar 232 insert 243 attaches to a face of the disk structure of the suspension disk 241. The span of the length of the outer dimension of the collar 232 insert 243 is lesser than the inner dimension of the collar 232 such that the collar 232 insert 243 inserts into the collar 232. The outer diameter of the suspension disk 241 is greater than the outer diameter of the collar 232 such that the collar 232 insert 243 is suspended within the collar 232 from the suspension disk 241. The spacer 212 is positioned between the suspension disk 241 and the collar 232 such that the spacer 212 separates the suspension disk 241 from the collar 232.

The collar 232 insert 243 further comprises a locking post 244. The locking post 244 is a prism-shaped structure. The locking post 244 mounts on the exterior lateral face of the prism structure of the collar 232 insert 243 such that the center axis of the locking post 244 projects radially away from the center axis of the collar 232 insert 243. The locking post 244 is sized such that the locking post 244 inserts through the locking aperture 233 of the collar 232 such that the position of the insert structure 213 is fixed relative to the canister cap 211.

The following definitions were used in this disclosure:
Align: As used in this disclosure, align refers to an arrangement of objects that are: 1) arranged in a straight plane or line; 2) arranged to give a directional sense of a plurality of parallel planes or lines; or, 3) a first line or curve is congruent to and overlaid on a second line or curve.

Anchor: As used in this disclosure, anchor means to hold an object firmly or securely.

Anchor Point: As used in this disclosure, an anchor point is a location to which a first object can be securely attached to a second object.

Ball Valve: As used in this disclosure, a ball valve is a type of commercially available check valve.

Canister: As used in this disclosure, a canister is a containment vessel configured for use in storing a fluid under pressure.

Cannula: As used in this disclosure, a cannula is a hollow tube that inserts into an object of the purpose of transferring fluids into and out of the object.

Center: As used in this disclosure, a center is a point that is: 1) the point within a circle that is equidistant from all the points of the circumference; 2) the point within a regular polygon that is equidistant from all the vertices of the regular polygon; 3) the point on a line that is equidistant from the ends of the line; 4) the point, pivot, or axis around which something revolves; or, 5) the centroid or first moment of an area or structure. In cases where the appropriate definition or definitions are not obvious, the fifth option should be used in interpreting the specification.

Center Axis: As used in this disclosure, the center axis is the axis of a cylinder or a prism. The center axis of a prism is the line that joins the center point of the first congruent face of the prism to the center point of the second corresponding congruent face of the prism. The center axis of a pyramid refers to a line formed through the apex of the pyramid that is perpendicular to the base of the pyramid. When the center axes of two cylinder, prism or pyramidal structures share the same line they are said to be aligned. When the center axes of two cylinder, prism or pyramidal structures do not share the same line they are said to be offset.

Chamber: As used in this disclosure, a chamber is an enclosed or enclosable negative space dedicated to a purpose.

Check Valve: As used in this disclosure, a check valve is a valve that permits the flow of fluid or gas in a single direction. Within selected potential embodiments of this disclosure, the check valve is a commercially available product that is selected from the group consisting of a ball valve and a Tesla valve.

Compression Spring: As used in this disclosure, a compression spring is a spring that resists forces attempting to compress the spring in the direction of the center axis of the spring. The compression spring will return to its original position when the compressive force is removed.

Congruent: As used in this disclosure, congruent is a term that compares a first object to a second object. Specifically, two objects are said to be congruent when: 1) they are geometrically similar; and, 2) the first object can superimpose over the second object such that the first object aligns, within manufacturing tolerances, with the second object.

Correspond: As used in this disclosure, the term correspond is used as a comparison between two or more objects wherein one or more properties shared by the two or more objects match, agree, or align within acceptable manufacturing tolerances.

Disk: As used in this disclosure, a disk is a prism-shaped object that is flat in appearance. Specifically, the sum of the surface areas of two ends of the prism-shaped object that forms the disk is greater than the surface area of the lateral face of the prism-shaped object that forms the disk. In this disclosure, the ends of the prism-shaped structure that forms the disk are referred to as the faces of the disk.

Fitting: As used in this disclosure, a fitting is a component that is attached to a first object. The fitting is used to forming a fluidic connection between the first object and a second object.

Fluid: As used in this disclosure, a fluid refers to a state of matter wherein the matter is capable of flow and takes the shape of a container it is placed within. The term fluid commonly refers to a liquid or a gas.

Fluidic Connection: As used in this disclosure, a fluidic connection refers to a tubular structure that transports a fluid from a first object to a second object. Methods to design and use a fluidic connection are well-known and documented in the mechanical, chemical, and plumbing arts.

Form Factor: As used in this disclosure, the term form factor refers to the size and shape of an object.

Gas: As used in this disclosure, a gas refers to a state (phase) of matter that is fluid and that fills the volume of the structure that contains it. Stated differently, the volume of a gas always equals the volume of its container.

Geometrically Similar: As used in this disclosure, geometrically similar is a term that compares a first object to a second object wherein: 1) the sides of the first object have a one to one correspondence to the sides of the second object; 2) wherein the ratio of the length of each pair of corresponding sides are equal; 3) the angles formed by the first object have a one to one correspondence to the angles of the second object; and, 4) wherein the corresponding angles are equal. The term geometrically identical refers to a situation where the ratio of the length of each pair of corresponding sides equals 1.

Hose: As used in this disclosure, a hose is a flexible hollow prism-shaped device used for transporting liquids and gases. When referring to a hose in this disclosure, the terms inner diameter and outer diameter are used as they would be used by those skilled in the plumbing arts.

Housing: As used in this disclosure, a housing is a rigid casing that encloses and protects one or more devices.

Inner Dimension: As used in this disclosure, the term inner dimension describes the span from a first inside or interior surface of a container to a second inside or interior surface of a container. The term is used in much the same way that a plumber would refer to the inner diameter of a pipe.

Liquid: As used in this disclosure, a liquid refers to a state (phase) of matter that is fluid and that maintains, for a given pressure, a fixed volume that is independent of the volume of the container.

Load: As used in this disclosure, the term load refers to an object upon which a force is acting or which is otherwise absorbing energy in some fashion. Examples of a load in this sense include, but are not limited to, a mass that is being moved a distance or an electrical circuit element that draws energy. The term load is also commonly used to refer to the forces that are applied to a stationary structure.

Load Path: As used in this disclosure, a load path refers to a chain of one or more structures that transfers a load generated by a raised structure or object to a foundation, supporting surface, or the earth.

Manifold: As used in this disclosure, a manifold is a pipe or chamber having several ports through which liquid or gas is gathered or distributed.

Negative Space: As used in this disclosure, negative space is a method of defining an object through the use of open or empty space as the definition of the object itself, or, through the use of open or empty space to describe the boundaries of an object.

Offset: As used in this disclosure, an offset refers to the span of distance or cant by which two objects are out of alignment.

One to One: When used in this disclosure, a one to one relationship means that a first element selected from a first set is in some manner connected to only one element of a second set. A one to one correspondence means that the one to one relationship exists both from the first set to the second set and from the second set to the first set. A one to one fashion means that the one to one relationship exists in only one direction.

Outer Dimension: As used in this disclosure, the term outer dimension describes the span from a first exterior or outer surface of a tube or container to a second exterior or outer surface of a tube or container. The term is used in much the same way that a plumber would refer to the outer diameter of a pipe.

Oxygen: As used in this disclosure, oxygen (CAS 7782-44-7) refers to the element with atomic number 8 in the periodic table. The chemical abbreviation for oxygen is 02. Oxygen is a diatomic element.

Patient: As used in this disclosure, a patient is a person who is designated to receive a medical treatment, therapy or service. The term patient may be extended to an animal when used within the context of the animal receiving veterinary treatment or services.

Perimeter: As used in this disclosure, a perimeter is one or more curved or straight lines that bounds an enclosed area on a plane or surface. The perimeter of a circle is commonly referred to as a circumference.

Plate: As used in this disclosure, a plate is a smooth, flat and semi-rigid or rigid structure that has at least one dimension that: a) is of uniform thickness; and b) that appears thin relative to the other dimensions of the object. Plates often have a rectangular appearance. Plates often have a disk-like structure. The face of the plate is a surface of the plate selected from the group consisting of: a) the surface of the plate with the greatest surface area; b) the surface of the plate that is distal from the surface of the plate with the greatest surface area. The edges of the plate comprise the surfaces of the plate that would not be considered faces as defined above. As defined in this disclosure, plates may be made of any material, but are commonly made of metal, plastic, and wood. When made of wood, a plate is often referred to as a board or a plank.

Pressure: As used in this disclosure, pressure refers to a measure of force per unit area.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Radial: As used in this disclosure, the term radial refers to a direction that: 1) is perpendicular to an identified central axis; or, 2) projects away from a center point.

Rigid Structure: As used in this disclosure, a rigid structure is a solid structure formed from an inelastic material that resists changes in shape. A rigid structure will permanently deform as it fails under a force.

Spring: As used in this disclosure, a spring is a device that is used to store mechanical energy. This mechanical energy will often be stored by: 1) deforming an elastomeric material that is used to make the device; 2) the application of a torque to a semi-rigid structure; or 3) a combination of the previous two items.

Suspend: As used in this disclosure, to suspend an object means to support an object such that the inferior end of the object does not form a significant portion of the load path of the object. Include inferior superior and load path.

Tube: As used in this disclosure, a tube is a hollow prism-shaped device formed with two open ends. The tube is used for transporting liquids and gases. The line that connects the center of the first congruent face of the prism to the center of the second congruent face of the prism is referred to as the center axis of the tube or the centerline of the tube. When two tubes share the same centerline they are said to be aligned. When the centerlines of two tubes are perpendicular to each other, the tubes are said to be perpendicular to each other. In this disclosure, the terms inner dimensions of a tube and outer dimensions of a tube are used as they would be used by those skilled in the plumbing arts.

U-Shaped Structure: As used in this disclosure, a U-shaped structure refers to a three-sided structure comprising a crossbeam, a first arm, and a second arm. In a U-shaped structure, the first arm and the second arm project away from the crossbeam: 1) in the same direction; 2) at a roughly perpendicular angle to the crossbeam, and, 3) the span of the length of the first arm roughly equals the span of the length of the second arm.

Valve: As used in this disclosure, a valve is a device that is used to control the flow of a fluid (gas or liquid) through a pipe.

With respect to the above description, it is to be realized that the optimum dimensional relationship for the various components of the invention described above and in FIGS. 1 through 7 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. An adapter for an oxygen delivery device comprising a canister adapter and a manual flow valve; wherein the canister adapter interfaces with a distribution apparatus;

wherein the distribution apparatus is a fluid transfer apparatus; wherein the manual flow valve is a plunger valve that attaches to the distribution apparatus; wherein the adapter for an oxygen delivery device is a mechanical structure; wherein the adapter for an oxygen delivery device is configured for use with a single oxygen canister; wherein the adapter for an oxygen delivery device attaches to the single oxygen canister; wherein the adapter for an oxygen delivery device is configured for use with the distribution apparatus; wherein the canister adapter interfaces with the distribution apparatus such that the distribution apparatus will receive oxygen from the single oxygen canister; wherein the distribution apparatus comprises a mask, a hose, and an oxygen connector; wherein the hose forms a fluidic connection between the oxygen connector and the single oxygen canister; wherein the oxygen connector forms a physical connection between the hose and the mask such that oxygen will flow from the hose into the mask;

wherein the canister adapter further comprises a canister cap, a spacer, and an insert structure;

wherein the spacer inserts between the canister cap and the insert structure; wherein the canister cap is a mechanical structure that adapts the canister adapter to the form factor of the single oxygen canister; wherein the canister cap forms a shell that attaches to the single oxygen canister;

wherein the canister cap attaches to the single oxygen canister such that the canister cap encloses the port fitting wherein the spacer is a mechanical structure; wherein the spacer is a disk-shaped structure; wherein the disk shape of the spacer has a u-shaped appearance; wherein the spacer separates the canister cap from the insert structure such that a span of an overall length of the canister adapter can be adjusted to match the specific form factor of the single oxygen canister.

2. The adapter for an oxygen delivery device according to claim 1 wherein the single oxygen canister is a high-pressure tank;

wherein the single oxygen canister contains oxygen under pressure;

wherein the single oxygen canister releases the oxygen into the canister adapter of the adapter for an oxygen delivery device.

3. The adapter for an oxygen delivery device according to claim 2 wherein the single oxygen canister further comprises a port fitting;

wherein the port fitting is a fitting that controls the flow of oxygen into and out of the single oxygen canister.

4. The adapter for an oxygen delivery device according to claim 3 wherein the manual flow valve controls the flow of oxygen through the distribution apparatus.

5. The adapter for an oxygen delivery device according to claim 4 wherein the manual flow valve is a manually controlled structure;

wherein the manual flow valve attaches to the oxygen connector such that the manual flow valve controls the flow of oxygen through the oxygen connector from the hose to the mask.

6. The adapter for an oxygen delivery device according to claim 5 wherein the canister adapter is a mechanical structure;

wherein the canister adapter forms a fluidic interface that attaches the distribution apparatus and the single oxygen canister.

7. The adapter for an oxygen delivery device according to claim 6 wherein the canister adapter mechanically attaches directly to the single oxygen canister;

wherein the canister adapter forms a fluidic connection with the single oxygen canister;

wherein the canister adapter forms a fluidic connection with the hose of the distribution apparatus.

8. The adapter for an oxygen delivery device according to claim 7 wherein the insert structure is a mechanical structure that attaches the canister cap to the distribution apparatus such that oxygen will flow from the port fitting through the canister cap and the insert structure into the distribution apparatus;

wherein the insert structure attaches to the canister cap by inserting into the canister cap.

9. The adapter for an oxygen delivery device according to claim 8 wherein the canister cap further comprises a cover, a collar, and a locking aperture;

wherein the cover and the locking aperture attach to the collar.

10. The adapter for an oxygen delivery device according to claim 9 wherein the insert structure further comprises a suspension disk, a supply fitting, and a collar insert;

wherein the supply fitting and the collar insert attach to the suspension disk.

11. The adapter for an oxygen delivery device according to claim 10 wherein the spacer is positioned between the suspension disk and the collar such that the spacer separates the suspension disk from the collar.

12. The adapter for an oxygen delivery device according to claim 11 wherein the cover is a dome-shaped structure;

wherein the cover is a hollow structure;

wherein the single oxygen canister inserts into the cover such that the cover encloses a portion of the single oxygen canister and fully encloses the port fitting;

wherein the collar is a prism-shaped structure;

wherein the collar is a tubular structure;

wherein the collar attaches the cover to the insert structure;

wherein the insert structure inserts into the collar to attach to the canister cap.

13. The adapter for an oxygen delivery device according to claim 12 wherein the locking aperture is an aperture that is formed through the lateral face of the prism structure of the collar;

wherein the locking aperture forms an anchor point to which the insert structure attaches to secure the insert structure to the canister cap.

14. The adapter for an oxygen delivery device according to claim 13 wherein the suspension disk is a plate structure;

wherein the suspension disk is a disk-shaped structure;

wherein the suspension disk forms the end of the insert structure that is distal from the single oxygen canister;

wherein the supply fitting is a fitting that forms the fluidic connection between the canister adapter and the hose of the distribution apparatus;

wherein the supply fitting mounts in the suspension disk such that the supply fitting is accessible from the exterior of the canister adapter.

15. The adapter for an oxygen delivery device according to claim 14
wherein the collar insert is a prism-shaped structure;
wherein the collar insert is a tubular structure;
wherein the collar insert is geometrically similar to the collar;
wherein the collar insert attaches to a face of the disk structure of the suspension disk;
wherein the span of the length of the outer dimension of the collar insert is lesser than the inner dimension of the collar such that the collar insert inserts into the collar;
wherein the outer diameter of the suspension disk is greater than the outer diameter of the collar such that the collar insert is suspended within the collar from the suspension disk.

16. The adapter for an oxygen delivery device according to claim 15
wherein the collar insert further comprises a locking post;
wherein the locking post is a prism-shaped structure;
wherein the locking post mounts on the exterior lateral face of the prism structure of the collar insert such that the center axis of the locking post projects radially away from the center axis of the collar insert;
wherein the locking post is sized such that the locking post inserts through the locking aperture of the collar such that the position of the insert structure is fixed relative to the canister cap.

\* \* \* \* \*